(12) United States Patent
Richardson

(10) Patent No.: US 11,369,616 B2
(45) Date of Patent: Jun. 28, 2022

(54) DRUG COMBINATION AND ITS USE IN THERAPY

(71) Applicant: Proximagen, LLC, Plymouth, MN (US)

(72) Inventor: Peter Richardson, Cambridge (GB)

(73) Assignee: PROXIMAGEN, LLC, Plymouth, MN (US)

( * ) Notice: Subject to any disclaimer, the term of this patent is extended or adjusted under 35 U.S.C. 154(b) by 0 days.

(21) Appl. No.: 16/127,363

(22) Filed: Sep. 11, 2018

(65) Prior Publication Data

US 2019/0000861 A1 Jan. 3, 2019

Related U.S. Application Data

(63) Continuation of application No. PCT/GB2017/050666, filed on Mar. 10, 2017.

(30) Foreign Application Priority Data

Mar. 11, 2016 (GB) .................................... 1604213

(51) Int. Cl.
| | |
|---|---|
| A61K 39/00 | (2006.01) |
| A61K 31/551 | (2006.01) |
| A61K 45/06 | (2006.01) |
| A61K 39/395 | (2006.01) |
| C07K 16/28 | (2006.01) |
| A61P 35/00 | (2006.01) |

(52) U.S. Cl.
CPC ...... *A61K 31/551* (2013.01); *A61K 39/39541* (2013.01); *A61K 45/06* (2013.01); *A61P 35/00* (2018.01); *C07K 16/2818* (2013.01)

(58) Field of Classification Search
CPC .. A61K 31/551; A61K 45/06; A61K 2300/00; A61P 35/00
See application file for complete search history.

(56) References Cited

U.S. PATENT DOCUMENTS

| 9,353,086 B2 * | 5/2016 | Savory ................. | C07D 405/14 |
| 2013/0289020 A1 | 10/2013 | Savory et al. | |
| 2014/0134142 A1 * | 5/2014 | Smith ................. | C07K 16/2803 |
| | | | 424/93.21 |
| 2015/0202291 A1 * | 7/2015 | Bosch .................... | A61K 35/15 |
| | | | 424/156.1 |
| 2015/0290207 A1 * | 10/2015 | Kutok ................. | A61K 31/495 |
| | | | 424/134.1 |

FOREIGN PATENT DOCUMENTS

| WO | WO 2012/049277 A1 | 4/2012 | |
| WO | WO-2012049277 A1 * | 4/2012 | ......... C07D 417/14 |
| WO | WO 2014/066532 | 5/2014 | |
| WO | WO-2014066532 A1 * | 5/2014 | ......... C07K 16/2803 |
| WO | WO 2015/019284 | 2/2015 | |
| WO | 2016157149 A1 | 10/2016 | |

OTHER PUBLICATIONS

Nelson et al., Ann. Intern Med. 2009; 151:727-737 (Year: 2009).*
Kataja et al., Ann Oncol 2009; 20(sup 4): iv10-14 (Year: 2009).*
Balmana et al. Ann Oncol 2009; 20(supp 4):iv19-20 (Year: 2009).*
The International Search Report and Written Opinion dated Jul. 6, 2017 in Application No. PCT/GB2017/050666.
Samit Chatterjee et al, "The Intricate Role of CXCR4 in Cancer" Immunotherapy of cancer: Advances in Cancer Research; ISSN 0065-230X; vol. 128, Jan. 1, 2014 (Jan. 1, 2014), Academic Press, US, XP055369748, ISSN: 0065-230X vol. 124, pp. 31-82, doi:10.1016/B978-0-12-411638-2.00002-1, abstract.
Indian Examination Report dated Jul. 15, 2020 by the Indian Patent Office for IN Application No. 201817034140, filed on Mar. 10, 2017 (Applicant—Proximagen, LLC) (6 Pages).
Dannussi-Joannopoulos, et al. (2002) "Efficacious immunomodulatory activity of the chemokine stromal cell-derived factor 1 (SDF-1): local secretion of SDF-1 at the tumor site serves as T-cell chemoattractant and mediates T-cell-dependent antitumor responses" *Blood* 100(5): 1551-8.
Bliss, C. I. (1939) "The Toxicity of Poisons Applied Jointly," from *Annals of Applied Biology*, pp. 585-615.
Feig, et al. (2013) "Targeting CXCL12 from FAP-expressing carcinoma-associated fibroblasts synergizes with anti-PD-L1 immunotherapy in pancreatic cancer" *Proc Natl Acad Sci USA* 110(50): 20212-7.
Fushimi, et al. (2006) "Adenoviral gene transfer of stromal cell-derived factor-1 to murine tumors induces the accumulation of dendritic cells and suppresses tumor growth" *Cancer Res.* 66(7): 3513-22.
Joyce and Fearon (2015) "T cell exclusion, immune privilege, and the tumor microenvironment" *Science* 348(6230): 74-80.
Kumar, et al. (2006) "CXCR4 physically associates with the T cell receptor to signal in T cells" *Immunity* 25(2): 213-24.
Mukherjee, et al. (2013) "The Role of chemokine receptor CXCR4 in breast cancer metastasis" *Am J Cancer Res* 3(1): 46-57.
Nomura, et al. (2001) "Enhancement of anti-tumor immunity by tumor cells transfected with the secondary lymphoid tissue chemokine EBI-1-ligand chemokine and stromal cell-derived factor-1alpha chemokine genes" *Int. J. Cancer* 91(5): 597-606.
Petraitis, et al. (2009) "Combination therapy in treatment of experimental pulmonary aspergillosis: in vitro and in vivo correlations of the concentration- and dose-dependent interactions between anidulafungin and voriconazole by Bliss independence drug interaction analysis" *Antimicrobial Agents and Chemotherapy* 53: 2382-2391.
Richardson (2016) "CXCR4 and Glioblastoma" *Anti-cancer agents in Med Chem* 16(1): 59-74.
Righi, et al. (2011) "CXCL12/CXCR4 blockade induces multimodal antitumor effects that prolong survival in an immunocompetent mouse model of ovarian cancer" *Cancer Res* 71(16): 5522-34.

(Continued)

*Primary Examiner* — Sheela J. Huff

(74) *Attorney, Agent, or Firm* — Ballard Spahr LLP

(57) ABSTRACT

The invention relates to a combination of CXCR4 antagonist 6-{4-[1-(Propan-2-yl)piperidin-4-yl]-1, 4-diazepan-1-yl}-N-(pyridin-4-yl)pyridine-2-carboxamide and an immune checkpoint inhibitor, and the use of the same in the treatment of tumours and/or cancers.

10 Claims, 1 Drawing Sheet

(56) References Cited

OTHER PUBLICATIONS

Williams, et al. (2010) "Multiple functions of CXCL12 in a syngeneic model of breast cancer" *Mol Cancer* 9: 250.
Wolchok, et al. (2013) "Nivolumab plus ipilimumab in advanced melanoma" *N Engl J Med* 369(2): 122-33.
Examination Report dated Apr. 10, 2019 by the European Patent Office for EP Application No. 17711296.8, filed on Mar. 10, 2017, and published as EP 3426682 on Jan. 16, 2019 (Applicant—Proximagen, LLC) (5 pages).
Examination Report dated Aug. 11, 2020 by the European Patent Office for EP Application No. 17711296.8, filed on Mar. 10, 2017, and published as EP 3426682 on Jan. 16, 2019 (Applicant—Proximagen, LLC) (3 pages).
Gajewski et al. (2013) "Innate and adaptive immune cells in the tumor microenvironment" Nature Immunol 14:1014-22.
Hamid et al. (2013) "Safety and tumor responses with lambrolizumab (anti-PD-1) in melanoma" N Engl J Med 369:134-44.
Office Action dated Dec. 9, 2020 by JP Patent Office for Patent Application No. 2018-566652, which was filed on Sep. 25, 2018 (Inventor—Richardson et al.; Applicant—Proximagen) (english translation 7 pages).

* cited by examiner

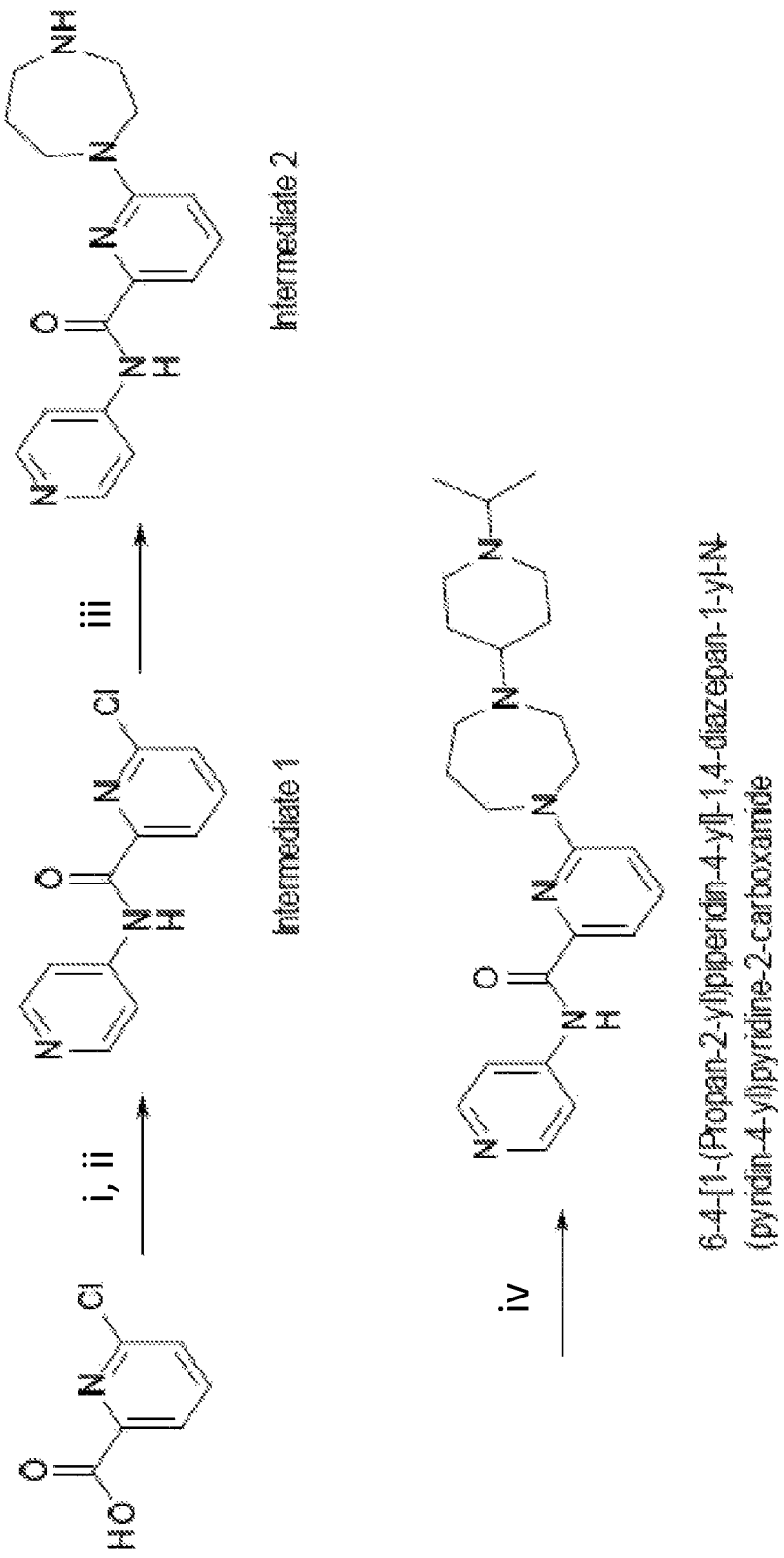

DRUG COMBINATION AND ITS USE IN THERAPY

The present application is a Continuation of International Application No. PCT/GB2017/050666 filed on Mar. 10, 2017 which claims the benefit of Great Britain Application No. 1604213.7 filed on Mar. 11, 2016, the contents of which are incorporated herein by reference.

FIELD OF THE INVENTION

This invention relates to a combination of CXCR4 antagonist 6-{4-[1-(Propan-2-yl)piperidin-4-yl]-1,4-diazepan-1-yl}-N-(pyridin-4-yl)pyridine-2-carboxamide and an immune checkpoint inhibitor, and the use of the same in the treatment of tumours and/or cancers, including the control and elimination of tumours.

BACKGROUND OF THE INVENTION

Cancer is a major cause of death which can in some cases be cured, especially if identified early in disease development. However the treatment of advanced cancers, particularly those with metastasis, remains poor. It has been recognised for many years that cancers are not controlled by the immune system, largely due to the immuno-suppressive environment of most tumours. This has led to the development of a wide range of mechanisms for assisting the immune system to control cancers. These include tumour targeted antibodies, vaccines, immune stimulating cytokines and the immune checkpoint inhibitors which have shown impressive results in the treatment of cancers, particularly melanoma (Hamid et al., *N Engl J Med* 2013; 369:134-44; Wolchok et al., *N Engl J Med.* 2013; 369(2):122-33). By blocking one or more of the immune checkpoints these inhibitors remove one of the "brakes" on the immune system and reduce the immunosuppressive environment of the tumours. Typical examples of these immune checkpoint inhibitors include monoclonal antibodies against CTLA-4, PD-1 and PD-L1. However a significant number of patients and cancer types do not respond (Joyce and Fearon, *Science* 2015; 348(6230):74-80), suggesting that other immunosuppressive mechanisms operate in tumours. This invention targets a range of these tumour associated immunosuppressive mechanisms, thus increasing the potency of the checkpoint inhibitors in the treatment of cancers.

CXCL12 (also referred to as SDF-1 or stromal derived factor-1) is a chemokine overexpressed in many tumours which activates the CXCR4 receptor located on the surface of cancer stem cells as well as many immune cells (Kumar et al., *Immunity.* 2006 25(2):213-24). Activation of this receptor has been implicated in the metastatic spread of many cancers (Mukherjee et al., *Am J Cancer Res.* 2013; 3(1): 46-57), in the formation of the tumour vasculature (Kozin et al., 2010; Kioi et al., 2010), and in both the recruitment and exclusion of immune cells from tumours (Feig et al., *Proc Natl Acad Sci USA.* 2013; 110(50):20212-7). It has been suggested that blockade of the CXCR4/CXCL12 axis would be beneficial in cancer treatment (Righi et al., *Cancer Res.* 2011; 71(16):5522-34; Vianello et al., *J Immunol.* 2006; 176(5):2902-14; Joyce and Fearon 2015; Richardson *Anti-cancer agents in Med. Chem* 2016 16(1): 59-74). However other studies suggest that SDF-1 promotes immunological control of tumour growth (Nomura et al., *Int J Cancer.* 2001; 91(5):597-606; Fushimi et al., *Cancer Res.* 2006; 66(7):3513-22; Williams et al., *Mol Cancer.* 2010; 9:250; and Dannussi-Joannopoulos et al., *Blood.* 2002; 100(5):1551-8).

The immunosuppressive environment of tumours is maintained by a number of different cell types including cancer associated fibroblasts (CAFs), M2 polarized tumour associated macrophages (TAMs) and regulatory T (Treg) cells. In addition there are few effector T (Teff) cells found in most tumours suggesting that the T cells either do not recognize the tumour cells as foreign, or they are excluded. T cells in tumours are frequently immunosuppressed, expressing checkpoint inhibitors (Gajewski et al., *Nature Immunol.* 2013 14:1014-22) and exhibiting anergy. Besides the CTLA-4 and PD-1/PDL1 inhibitors other checkpoint inhibitors could be used to help reverse this immunosuppression, including LAG3, TIM-3, KIR and CD160. In addition Feig et al., 2013 reported that CXCL12 may be the means by which some tumours exclude T cells, although others have reported that CXCL12 may attract T cells (e.g. Nomura et al., 2001). The source of this CXCL12 is probably the CAFs and tumour endothelial cells which secrete large amounts of CXCL12. This chemokine while influencing T cell migration also promotes the M2 polarization of TAMs resulting in increased IDO-1 activity and secretion of IL-10, both of which are powerful immunosuppressant mechanisms.

SUMMARY OF THE INVENTION

The present invention relates to a method of augmenting the control and elimination of tumours by immune checkpoint inhibitors through inhibition of CXCR4, by administering to a patient a pharmaceutically effective amount of CXCR4 antagonist 6-{4-[1-(Propan-2-yl)piperidin-4-yl]-1,4-diazepan-1-yl}-N-(pyridin-4-yl)pyridine-2-carboxamide in combination with an immune checkpoint inhibitor. Without wishing to be bound by theory, it is believed that the beneficial effect of the CXCR4 antagonist results from blockade of CXCR4/CXCL12 signalling. This is expected to result in the accumulation of effector T cells (CD8+ and CD4+) in tumours, while inducing a reduction in the recruitment of Treg cells (both FoxP3+ and FoxP3−) and myeloid derived suppressor calls, as well as reversing the M2 polarization of tumour associated macrophages. This is expected to relieve the immunosuppression induced by Treg cells, myeloid-derived suppressor cells (MDSCs) and tumour associated macrophages.

6-{4-[1-(Propan-2-yl)piperidin-4-yl]-1,4-diazepan-1-yl}-N-(pyridin-4-yl)pyridine-2-carboxamide is suitable for use in combination with any immune checkpoint inhibitors, and with other immune stimulating agents including engineered chimeric antigen receptor (CAR) T cells, vaccines and anti-tumour antibodies. Suitable because therapeutic approaches based on immune checkpoint inhibitors, immune stimulating agents including engineered chimeric antigen receptor (CAR) T cells, vaccines and anti-tumour antibodies are expected to be enhanced by a reduction in the immunosuppressive environment of tumours.

In preliminary experimental studies it has been surprisingly found that a combination of CXCR4 antagonist 6-{4-[1-(Propan-2-yl)piperidin-4-yl]-1,4-diazepan-1-yl}-N-(pyridin-4-yl)pyridine-2-carboxamide and an immune checkpoint inhibitor shows a synergistic effect in reducing tumour growth in a suitable animal model. The preliminary studies indicate that the effect of the 6-{4-[1-(Propan-2-yl) piperidin-4-yl]-1,4-diazepan-1-yl}-N-(pyridin-4-yl)pyridine-2-carboxamide and an immune checkpoint inhibitor is surprisingly potent and greater than the sum of the individual drugs, suggesting that the combination has a substantially improved effect. Consequently, a considerably reduced dose of both drugs can be given for an equivalent effect for each individual drug, thus reducing side-effects and drug burden.

Any suitable form of the 6-{4-[1-(Propan-2-yl)piperidin-4-yl]-1,4-diazepan-1-yl}-N-(pyridin-4-yl)pyridine-2-carboxamide and immune checkpoint inhibitor can be used. These include salts, solvates, prodrugs and active metabolites thereof.

Thus, in an embodiment the present makes available a combination of CXCR4 antagonist 6-{4-[1-(Propan-2-yl)piperidin-4-yl]-1,4-diazepan-1-yl}-N-(pyridin-4-yl)pyridine-2-carboxamide and an immune checkpoint inhibitor. The combination is expected to be surprisingly effective in the treatment of a tumour. The immune checkpoint inhibitor may be an inhibitor of a target selected from any one of the group consisting of CTLA-4, PD-1, PD-L1, PDL2, LAG3, TIM-3, KIR, CD160, B7-H3 (CD276), BTLA (CD272), IDO (Indoleamine 2,3-dioxygenase), adenosine A2A receptor, and C10ORF54. Preferred immune checkpoint inhibitors inhibit CTLA-4 or PD-1. Particularly preferred immune checkpoint inhibitors inhibit PD-1. The immune checkpoint inhibitor may be an antibody selected from anti-CTLA-4, anti-PD-1, anti-PDL1, anti-PDL2, anti-LAG3, anti-TIM-3, anti-KIR, anti-CD160, anti-B7-H3 (CD276), anti-BTLA (CD272), anti-IDO (Indoleamine 2,3-dioxygenase), anti-adenosine A2A receptor, and anti-C10ORF54. The immune checkpoint inhibitor may be an anti-CTLA-4 or anti-PD-1 antibody. Particularly preferred may be an anti-PD-1 antibody. The immune checkpoint inhibitor may be a monoclonal antibody, a humanized antibody, a fully human antibody, a fusion protein or a combination thereof. Exemplary immune checkpoint inhibitors include Durvalumab (MEDI4736), Atezolizumab (MPDL3280A), Avelumab (MSB0010718C), BMS936559/MDX1105, Tremelimumab, Ipilimumab, Pembrolizumab, Nivolumab, Pidilizumab, BMS986016, and Iirilumab. Preferred examples of checkpoint inhibitors include anti-PD-1 and anti-CTLA-4 monoclonal antibodies such as Pembrolizumab (Keytruda®), Nivolumab (Opdivo®), and Ipilimumab (Yervoy®).

In an alternative embodiment, the present invention makes available a product comprising a combination of 6-{4-[1-(Propan-2-yl)piperidin-4-yl]-1,4-diazepan-1-yl}-N-(pyridin-4-yl)pyridine-2-carboxamide and an immune checkpoint inhibitor as a combined preparation for simultaneous, sequential or separate use in treating a tumour.

In another embodiment, the present invention makes available 6-{4-[1-(Propan-2-yl)piperidin-4-yl]-1,4-diazepan-1-yl}-N-(pyridin-4-yl)pyridine-2-carboxamide for use in treating a tumour wherein an immune checkpoint inhibitor is administered simultaneously, separately or sequentially with 6-{4-[1-(Propan-2-yl)piperidin-4-yl]-1,4-diazepan-1-yl}-N-(pyridin-4-yl)pyridine-2-carboxamide.

In another embodiment, the present invention makes available a method of preventing or treating a tumour and/or cancer, comprising administering to a human or animal subject in need thereof 6-{4-[1-(Propan-2-yl)piperidin-4-yl]-1,4-diazepan-1-yl}-N-(pyridin-4-yl)pyridine-2-carboxamide in any suitable form and an immune checkpoint inhibitor in sufficient amounts to provide a therapeutic effect. The tumour and/or cancer may include cancers of the oesophagus, colon and rectum, breast, lung, endometrium, pancreas, skin, liver, bladder, kidney, gall bladder and ovary. In a preferred embodiment, the tumour may be a colorectal, breast, or liver cancer, or it may be a melanoma. 6-{4-[1-(Propan-2-yl)piperidin-4-yl]-1,4-diazepan-1-yl}-N-(pyridin-4-yl)pyridine-2-carboxamide and the immune checkpoint inhibitor may be administered simultaneously, separately or sequentially in any order.

The therapeutic effect may be provided by several dosage regimens. The dose of 6-{4-[1-(Propan-2-yl)piperidin-4-yl]-1,4-diazepan-1-yl}-N-(pyridin-4-yl)pyridine-2-carboxamide that is administered with the immune checkpoint inhibitor will of course depend on the usual factors, but is preferably at least 0.2, e.g. at least 1, and may be up to 40 or 50 mg/kg/day. In an embodiment the dose of 6-{4-[1-(Propan-2-yl)piperidin-4-yl]-1,4-diazepan-1-yl}-N-(pyridin-4-yl)pyridine-2-carboxamide is from 5 to 100 mg/day. Preferably the dose may be from 10 to 90 mg/day. More preferably the dose may be from 20 to 80 mg/day. Most preferably the dose may be from 30 to 70 mg/day. The dose may be given in any suitable form, for instance orally, by injection, intravenously, by inhalation, by suppository or applied topically. The dose may be given 5 times per week.

The dose of the immune checkpoint inhibitor that is administered with 6-{4-[1-(Propan-2-yl)piperidin-4-yl]-1,4-diazepan-1-yl}-N-(pyridin-4-yl)pyridine-2-carboxamide will of course depend on the usual factors, including its potency, but is preferably at least 0.2, and may be up to 10 mg/kg/day. Preferably the dose may be from 0.2 to 3 mg/kg/day. More preferably the dose may be from 0.5 to 3 mg/kg/day. The dose may be given in any suitable form, for instance orally, by injection, intravenously, by inhalation, by suppository or applied topically. The dose may be given 3 times per week for three weeks or once every three days. The immune checkpoint inhibitor used in the dosage regimen may be an antibody. The immune checkpoint inhibitor used in the dosage regimen may be preferably an inhibitor of PD1 or CTLA4, more preferably an anti-PD1 or anti-CTLA4 antibody, and most preferably an anti-PD1 antibody. Most preferably, an anti-PD1 antibody may be used in the dosage regimen. For the dosage regimen all possible and preferred combinations of dosages of 6-{4-[1-(Propan-2-yl)piperidin-4-yl]-1,4-diazepan-1-yl}-N-(pyridin-4-yl)pyridine-2-carboxamide and immune checkpoint inhibitor as listed above may be envisaged. For instance at least 0.2 and up to 50 mg/kg/day of 6-{4-[1-(Propan-2-yl)piperidin-4-yl]-1,4-diazepan-1-yl}-N-(pyridin-4-yl)pyridine-2-carboxamide may be administered, simultaneously, separately or sequentially with at least 0.2 and up to 10 mg/kg/day of an immune checkpoint inhibitor. At least 0.2 and up to 50 mg/kg/day of 6-{4-[1-(Propan-2-yl)piperidin-4-yl]-1,4-diazepan-1-yl}-N-(pyridin-4-yl)pyridine-2-carboxamide may be administered, simultaneously, separately or sequentially with at least 0.2 and up to 10 mg/kg/day of an antibody. At least 0.2 and up to 50 mg/kg/day of 6-{4-[1-(Propan-2-yl)piperidin-4-yl]-1,4-diazepan-1-yl}-N-(pyridin-4-yl)pyridine-2-carboxamide may be administered, simultaneously, separately or sequentially with at least 0.2 and up to 10 mg/kg/day of an inhibitor of PD1 or CTLA4, preferably an anti-PD1 or anti-CTLA4 antibody. At least 0.2 and up to 50 mg/kg/day of 6-{4-[1-(Propan-2-yl)piperidin-4-yl]-1,4-diazepan-1-yl}-N-(pyridin-4-yl)pyridine-2-carboxamide may be administered, simultaneously, separately or sequentially with at least 0.2 and up to 10 mg/kg/day of an anti-PD1 antibody.

The inventors have surprisingly found that the level of expression of the chemokine SDF-1 (CXCL12) in cancer cells can be used to identify patients having cancer who are likely to respond to treatment with a therapeutically effective amount of 6-{4-[1-(Propan-2-yl)piperidin-4-yl]-1,4-diazepan-1-yl}-N-(pyridin-4-yl)pyridine-2-carboxamide in any suitable form and an immune checkpoint inhibitor.

Specifically, increased levels of SDF-1 in a sample from a patient having colorectal, breast or liver cancer, or melanoma may be used to identify whether that patient will respond to treatment with 6-{4-[1-(Propan-2-yl)piperidin-4-yl]-1,4-diazepan-1-yl}-N-(pyridin-4-yl)pyridine-2-carboxamide in any suitable form and an immune checkpoint inhibitor.

Thus, in an embodiment, the invention concerns a method of treating or preventing a tumour and/or cancer comprising: determining whether a tissue sample from a human or animal subject has a high level of SDF-1; and selectively administering to the human or animal subject in need thereof 6-{4-[1-(Propan-2-yl)piperidin-4-yl]-1,4-diazepan-1-yl}-N-(pyridin-4-yl)pyridine-2-carboxamide in any suitable form and an immune checkpoint inhibitor in sufficient amounts to provide a therapeutic effect, based on said tissue sample having been previously determined to have a high level of SDF-1. The tissue sample may be a tumour or a portion thereof. A high level of SDF-1 may be at least 3 FPKM. A high level of SDF-1 may be at least 4, or at least 10, or at least 11, or at least 12, or at least 13, or at least 14, or at least 15, or at least 16 FPKM. A high level of SDF-1 may be at least 17, or at least 26 or at least 42 FPKM. In an embodiment, the invention concerns the treatment of tumours with 6-{4-[1-(Propan-2-yl)piperidin-4-yl]-1,4-diazepan-1-yl}-N-(pyridin-4-yl)pyridine-2-carboxamide and an immune checkpoint inhibitor, the tumours having high levels of CXCL12 (SDF-1), including cancers of the oesophagus, colon and rectum, breast, lung, endometrium, pancreas, skin, liver, bladder, kidney, gall bladder and ovary. In a particularly preferred embodiment, the tumour having a high level of SDF-1 may be a colorectal, breast, or liver cancer, or it may be a melanoma.

In an embodiment, treatment with 6-{4-[1-(Propan-2-yl)piperidin-4-yl]-1,4-diazepan-1-yl}-N-(pyridin-4-yl)pyridine-2-carboxamide increases the sensitivity of the cancer cells to the host immune responses, or reduces immune suppression in the tumour.

In an embodiment, treatment with 6-{4-[1-(Propan-2-yl)piperidin-4-yl]-1,4-diazepan-1-yl}-N-(pyridin-4-yl)pyridine-2-carboxamide and an immune checkpoint inhibitor inhibits cancer cell growth.

In an embodiment, treatment with 6-{4-[1-(Propan-2-yl)piperidin-4-yl]-1,4-diazepan-1-yl}-N-(pyridin-4-yl)pyridine-2-carboxamide and an immune checkpoint inhibitor eliminates cancer cells.

In an embodiment, treatment with 6-{4-[1-(Propan-2-yl)piperidin-4-yl]-1,4-diazepan-1-yl}-N-(pyridin-4-yl)pyridine-2-carboxamide and an immune checkpoint inhibitor reduces tumour mass.

In an embodiment, 6-{4-[1-(Propan-2-yl)piperidin-4-yl]-1,4-diazepan-1-yl}-N-(pyridin-4-yl)pyridine-2-carboxamide and an immune checkpoint are used to treat a tumour, wherein the tumour is resistant to immunotherapy.

BRIEF DESCRIPTION OF THE DRAWINGS

FIG. 1 depicts the synthetic Route for preparation of 6-{4-[1-(Propan-2-yl)piperidin-4-yl]-1,4-diazepan-1-yl}-N-(pyridin-4-yl)pyridine-2-carboxamide, wherein (i) is (COCL)2, DMF, DCM, (ii) is homopiperazine, DMA, 180C, microwave, and (iv) NABH(OAc)3, 1-(propan-2-yl)piperidin-4-one, DCM.

Preparation of 6-{4-[1-(Propan-2-yl)piperidin-4-yl]-1,4-diazepan-1-yl}-N-(pyridin-4-yl)pyridine-2-carboxamide WO2012/049277 teaches the structure and preparation of CXCR4 antagonist 6-{4-[1-(Propan-2-yl)piperidin-4-yl]-1, 4-diazepan-1-yl}-N-(pyridin-4-yl)pyridine-2-carboxamide, which is Example 30, and has the structure:

6-{4-[1-(Propan-2-yl)piperidin-4-yl]-1,4-diazepan-1-yl}-N-(pyridin-4-yl)pyridine-2-carboxamide may be prepared using techniques known to the skilled person, including, for example, the method set out in FIG. 1.

The following abbreviations have been used:
Aq aqueous
d day(s)
DCM dichloromethane
DIPEA diisopropylethylamine
DMA dimethylacetamide
DMF dimethylformamide
DMSO dimethyl sulfoxide
ES$^+$ electrospray ionization
h hour(s)
HPLC High Performance Liquid Chromatography
IR Infrared Spectroscopy
LCMS Liquid Chromatography Mass Spectrometry
MeCN acetonitrile
[MH]$^+$ protonated molecular ion
min minute(s)
MS Mass Spectrometry
NMR Nuclear Magnetic Spectrometry
RP reverse phase
Rt retention time
sat saturated
TFA trifluoroacetic acid
UPLC Ultra Performance Liquid Chromatography Experimental Methods All reagents were commercial grade and were used as received without further purification, unless otherwise specified. Reagent grade solvents were used, unless otherwise specified. The reactions facilitated by microwave heating were performed on a Biotage Initiator system. Preparative low pressure chromatography was performed using a CombiFlash Companion or Combiflash RF systems equipped with RediSep or GraceResolv silica and C18 reverse phase columns. Preparative reverse phase HPLC was performed on a Gilson system with a UV detector equipped with a ACE-5AQ, 100×21.20 mm, 5 mm or Phenomenex Synergi Hydro-RP 80A AXIA, 100×21.20 mm, 4 mm columns. The purest fractions were collected, concentrated and dried under vacuum. Compounds were typically dried in a vacuum oven between 40° C. and 60° C. prior to purity analysis. Analytical HPLC was performed on an Agilent 1100 system. Analytical LCMS was performed on an Agilent 1100 HPLC system with a Waters ZQ mass spectrometer. NMR was performed on a Bruker Avance 500 MHz Cryo Ultrashield with Dual CryoProbe. IR analysis was performed on a Perkin Elmer FT-IR Spectrum BX using a Pike MIRacle single reflection ATR. Melting point determination was performed on a Reichert Thermovar hotstage microscope. Reactions were performed at room temperature unless otherwise stated. The compounds were automatically named using IUPAC rules.

Intermediate 1

6-Chloro-N-(pyridin-4-yl)pyridine-2-carboxamide

6-Chloropyridine-2-carboxylic acid (5.50 g, 34.9 mmol) and DMF (0.5 mL) were dissolved in DCM (100 mL) and oxalyl chloride (7.09 mL, 83.8 mmol) was added. The reaction mixture was stirred for 0.5 h then the solvents were removed in vacuo. The residue was dissolved in DCM (100 mL) cooled to 0° C. DIPEA (14.6 mL, 83.8 mmol) and 4-aminopyridine (3.94 g, 41.9 mmol) were added and the reaction was allowed to warm to room temperature then stirred for a further 0.5 h. The solvents were removed in vacuo and the residue was partitioned between DCM (100 mL) and water (75 mL). The aqueous layer was extracted with DCM (2×75 mL), the organic layers combined, washed with $Na_2CO_3$ (1M, 75 mL), brine (75 mL), dried ($MgSO_4$) and the solvents removed in vacuo. The residue was purified by column chromatography to give the title compound (6.66 g, 81.7%) as an off white solid. LCMS ($ES^+$): 234.2 $[MH]^+$.

Intermediate 2

6-(1,4-Diazepan-1-yl)-N-(pyridin-4-yl)pyridine-2-carboxamide

Intermediate 1 (1.5 g, 6.42 mmol) was dissolved in DMA (12.5 mL). Homopiperazine (3.22 g, 32.1 mmol) was added and the reaction mixture was heated using a Biotage microwave at 180° C. for 0.5 h. This process was repeated three further times on the same scale and the four batches were combined and the solvent removed in vacuo. The residue was dissolved in DCM (300 mL) and washed with sat aq $Na_2CO_3$ solution (150 mL), brine (100 mL), dried ($MgSO_4$) and the solvents were removed in vacuo. The residue was purified by column chromatography to give the title compound (6.88 g, 90.1%) as light yellow solid. LCMS ($ES^+$): 298.2 $[MH]^+$.

6-{4-[1-(Propan-2-yl)piperidin-4-yl]-1,4-diazepan-1-yl}-N-(pyridin-4-yl)pyridine-2-carboxamide Intermediate 2 (4.88 g, 16.4 mmol) was dissolved in DCM (200 mL). 1-(Propan-2-yl)piperidin-4-one (4.88 mL, 32.8 mmol) and sodium triacetoxyborohydride (17.4 g, 82.1 mmol) were added and the reaction mixture stirred for 20 h. The reaction mixture was diluted with DCM (200 mL) and quenched with sat aq $Na_2CO_3$ solution (100 mL). The aqueous layer was extracted with DCM (100 mL). The organic layers were combined, washed with brine (50 mL), dried ($MgSO_4$) and the solvents removed in vacuo. The residue was purified by crystallisation from MeCN followed by reverse phase column chromatography. The residue was partitioned between DCM (300 mL) and sat aq $Na_2CO_3$ solution (100 mL). The aqueous layer was extracted with DCM (50 mL) and the organic layers were combined, washed with brine (50 mL), dried ($MgSO_4$) and the solvents removed in vacuo. The residue was crystallised from MeCN to give the title compound (4.66 g, 67.3%) as a light yellow solid.

HPLC: Rt 3.47 min, 100% purity

LCMS ($ES^+$): 423.2 $[MH]^+$ $^1$H NMR (500 MHz, DMSO-$d_6$) $\delta_H$ 10.31 (1H, s, N$\underline{H}$), 8.52-8.50 (2H, m, Ar$\underline{H}$), 7.84-7.82 (2H, m, Ar$\underline{H}$), 7.70 (1H, dd, J 8.5 and 7.3 Hz, Ar$\underline{H}$), 7.30 (1H, d, J 7.2 Hz, Ar$\underline{H}$), 6.93 (1H, d, J 8.7 Hz, Ar$\underline{H}$), 3.80 (2H, m, NC$\underline{H}_2$), 3.76 (2H, m, NC$\underline{H}_2$), 2.82-2.79 (2H, m, NC$\underline{H}_2$), 2.77-2.73 (2H, m, NC$\underline{H}_2$), 2.62 (1H, spt, J 6.6 Hz, C$\underline{H}$Me), 2.58-2.56 (2H, m, NC$\underline{H}_2$), 2.39-2.33 (1H, m, NC$\underline{H}$C$\underline{H}_2$), 2.05-1.88 (2H, m, NC$\underline{H}_2$), 1.85-1.78 (2H, m, C$\underline{H}_2$), 1.65-1.60 (2H, m, NCHC$\underline{H}_2$), 1.36 (2H, qd, J 11.7 and 3.4 Hz, NCHC$\underline{H}_2$), 0.91 (6H, d, J 6.6 Hz, CH(C$\underline{H}_3$)$_2$)

IR (solid) $v_{max}$/cm$^{-1}$ 3328, 2936, 2358, 2162, 1982, 1682, 1597, 1582, 1510, 1485, 1459, 1418, 1404, 1383, 1364, 1336, 1282, 1246, 1211, 1179, 1161, 1125, 1070, 1030, 994, 972, 926, 898, 878, 824, 814, 758, 681 and 617

Melting point: 157-159° C.

DESCRIPTION OF THE INVENTION

The invention is concerned with immune checkpoint inhibitors. Certain cells of the immune system have "checkpoint" proteins which need to be activated (or inactivated) to start an immune response. Cancer cells sometimes develop resistance by finding ways to use these checkpoints to avoid being attacked by the immune system. The term "immune checkpoint inhibitor", as used herein is a molecule which targets an immune checkpoint in order to prevent deactivation of the immune system response. Any suitable checkpoint inhibitor is within the scope of the invention. Examples of checkpoints include PD-1 and CTLA-4. Checkpoint inhibitors include antibodies, such as anti-PD-1 and anti-CTLA-4. Examples of checkpoint inhibitors include Pembrolizumab (Keytruda®), Nivolumab (Opdivo®), and Ipilimumab (Yervoy®).

As used herein, the term "tumour" is taken to mean a proliferation of heterogeneous cells, collectively forming a mass of tissue in a subject resulting from the abnormal proliferation of malignant cancer cells.

Any suitable form of the 6-{4-[1-(Propan-2-yl)piperidin-4-yl]-1,4-diazepan-1-yl}-N-(pyridin-4-yl)pyridine-2-carboxamide and immune checkpoint inhibitor can be used. These include salts, prodrugs and active metabolites thereof. Suitable dose ranges for the 6-{4-[1-(Propan-2-yl)piperidin-4-yl]-1,4-diazepan-1-yl}-N-(pyridin-4-yl)pyridine-2-carboxamide and immune checkpoint inhibitor are disclosed herein. The synergistic effect of the combination means that the effective dose may be reduced.

As used herein the term "salt" includes base addition, acid addition and ammonium salts. 6-{4-[1-(Propan-2-yl)piperidin-4-yl]-1,4-diazepan-1-yl}-N-(pyridin-4-yl)pyridine-2-carboxamide is basic and so can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, trifluoroacetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds which have a basic nitrogen can also form quaternary ammonium salts with a pharmaceutically acceptable counter-ion such as chloride, bromide, acetate, formate, p-toluenesulfonate, succinate, hemi-succinate, naphthalene-bis sulfonate, methanesulfonate, trifluoroacetate, xinafoate, and the like. For a review on salts, see Handbook of Pharmaceutical Salts: Properties, Selection, and Use by Stahl and Wermuth (Wiley-VCH, Weinheim, Germany, 2002).

The compound "6-{4-[1-(Propan-2-yl)piperidin-4-yl]-1,4-diazepan-1-yl}-N-(pyridin-4-yl)pyridine-2-carboxamide" may exist as a solvate. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

The compound "6-{4-[1-(Propan-2-yl)piperidin-4-yl]-1,4-diazepan-1-yl}-N-(pyridin-4-yl)pyridine-2-carboxamide" may exist in an amorphous form and/or several polymorphic forms and may be obtained in different crystal habits. Any reference herein to 6-{4-[1-(Propan-2-yl)piperidin-4-yl]-1,4-diazepan-1-yl}-N-(pyridin-4-yl)pyridine-2-carboxamide includes all forms of that compound irrespective of amorphous or polymorphic form.

The dose of 6-{4-[1-(Propan-2-yl)piperidin-4-yl]-1,4-diazepan-1-yl}-N-(pyridin-4-yl)pyridine-2-carboxamide that is administered with the immune checkpoint inhibitor will of course depend on the usual factors, but is preferably at least 0.2, e.g. at least 1, and may be up to 40 or 50 mg/kg/day. In an embodiment the dose of 6-{4-[1-(Propan-2-yl)piperidin-4-yl]-1,4-diazepan-1-yl}-N-(pyridin-4-yl)pyridine-2-carboxamide is from 5 to 100 mg/day. Preferably the dose may be from 10 to 90 mg/day. More preferably the dose may be from 20 to 80 mg/day. Most preferably the dose may be from 30 to 70 mg/day. The dose may be given in any suitable form, for instance orally, by injection, intravenously, by inhalation, by suppository or applied topically. The dose may be given 5 times per week.

The dose of the immune checkpoint inhibitor that is administered with 6-{4-[1-(Propan-2-yl)piperidin-4-yl]-1,4-diazepan-1-yl}-N-(pyridin-4-yl)pyridine-2-carboxamide will of course depend on the usual factors, including its potency, but is preferably at least 0.2, and may be up to 10 mg/kg/day. Preferably the dose is from 0.2 to 3 mg/kg/day. More preferably the dose is from 0.5 to 3 mg/kg/day. The dose may be given in any suitable form, for instance orally, by injection, intravenously, by inhalation, by suppository or applied topically. The dose may be given 3 times per week for three weeks or once every three days. The immune checkpoint inhibitor used in the dosage regimen may be an antibody. The immune checkpoint inhibitor used in the dosage regimen may be preferably an inhibitor of PD1 or CTLA4, more preferably an anti-PD1 or anti-CTLA4 antibody, and most preferably an anti-PD1 antibody. Most preferably, an anti-PD1 antibody may be used in the dosage regimen. For the dosage regimen all possible and preferred combinations of dosages of 6-{4-[1-(Propan-2-yl)piperidin-4-yl]-1,4-diazepan-1-yl}-N-(pyridin-4-yl)pyridine-2-carboxamide and immune checkpoint inhibitor as listed above may be envisaged. For instance at least 0.2 and up to 50 mg/kg/day of 6-{4-[1-(Propan-2-yl)piperidin-4-yl]-1,4-diazepan-1-yl}-N-(pyridin-4-yl)pyridine-2-carboxamide may be administered, simultaneously, separately or sequentially with at least 0.2 and up to 10 mg/kg/day of an immune checkpoint inhibitor. At least 0.2 and up to 50 mg/kg/day of 6-{4-[1-(Propan-2-yl)piperidin-4-yl]-1,4-diazepan-1-yl}-N-(pyridin-4-yl)pyridine-2-carboxamide may be administered, simultaneously, separately or sequentially with at least 0.2 and up to 10 mg/kg/day of an antibody. At least 0.2 and up to 50 mg/kg/day of 6-{4-[1-(Propan-2-yl)piperidin-4-yl]-1,4-diazepan-1-yl}-N-(pyridin-4-yl)pyridine-2-carboxamide may be administered, simultaneously, separately or sequentially with at least 0.2 and up to 10 mg/kg/day of an inhibitor of PD1 or CTLA4, preferably an anti-PD1 or anti-CTLA4 antibody. At least 0.2 and up to 50 mg/kg/day of 6-{4-[1-(Propan-2-yl)piperidin-4-yl]-1,4-diazepan-1-yl}-N-(pyridin-4-yl)pyridine-2-carboxamide may be administered, simultaneously, separately or sequentially with at least 0.2 and up to 10 mg/kg/day of an anti-PD1 antibody.

The CXCR4 antagonist and checkpoint inhibitors of the invention may be administered by any available route, such as via the oral, inhaled, intranasal, sublingual, intravenous, intramuscular, rectal, dermal, and vaginal routes. The CXCR4 antagonist is preferably administered via the oral or intravenous route. The checkpoint inhibitor is preferably administered via the intravenous or intramuscular route. In an embodiment, the 6-{4-[1-(Propan-2-yl)piperidin-4-yl]-1,4-diazepan-1-yl}-N-(pyridin-4-yl)pyridine-2-carboxamide is administered orally or intravenously and the checkpoint inhibitor(s) is administered intravenously.

The 6-{4-[1-(Propan-2-yl)piperidin-4-yl]-1,4-diazepan-1-yl}-N-(pyridin-4-yl)pyridine-2-carboxamide is preferably formulated to be administered orally, for example as tablets, troches, lozenges, aqueous or oral suspensions, dispersible powders or granules. Preferred pharmaceutical compositions comprising 6-{4-[1-(Propan-2-yl)piperidin-4-yl]-1,4-diazepan-1-yl}-N-(pyridin-4-yl)pyridine-2-carboxamide are tablets and capsules. Liquid dispersions for oral administration may be syrups, emulsions and suspensions. Alternatively, the 6-{4-[1-(Propan-2-yl)piperidin-4-yl]-1,4-diazepan-1-yl}-N-(pyridin-4-yl)pyridine-2-carboxamide may be formulated as a pressed tablet or capsule with conventional excipients, examples of which are given below. These may be immediate release or modified, sustained or controlled release preparations.

Compositions intended for oral use may be prepared according to any method known to the art for the manufacture of pharmaceutical compositions, and such compositions may contain one or more agents selected from the group consisting of sweetening agents, flavouring agents, colouring agents and preserving agents in order to provide pharmaceutically elegant and palatable preparations. Tablets contain the 6-{4-[1-(Propan-2-yl)piperidin-4-yl]-1,4-diazepan-1-yl}-N-(pyridin-4-yl)pyridine-2-carboxamide in admixture with non-toxic pharmaceutically acceptable excipients which are suitable for the manufacture of tablets. These excipients may include but are not restricted to, inert diluents, such as calcium carbonate, sodium carbonate, lactose, calcium phosphate or sodium phosphate; granulating and disintegrating agents, for example corn starch or alginic acid; binding agents, for example starch gelatin, acacia, microcrystalline cellulose or polyvinyl pyrrolidone; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate, or glyceryl distearate may be employed.

Aqueous suspensions may contain the 6-{4-[1-(Propan-2-yl)piperidin-4-yl]-1,4-diazepan-1-yl}-N-(pyridin-4-yl)pyridine-2-carboxamide and checkpoint inhibitor(s) in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long-chain aliphatic alcohols, for example heptadecaethyleneoxycetanol, or condensation products of ethylene oxide with partial esters derived from fatty acids, for example polyoxyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, polyoxyethylene hydrogenated castor oil, fatty acids such as oleic acid, or in a mineral oil such as liquid paraffin or in other surfactants or detergents. The oily suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid.

Dispersible powders and granules suitable for preparation of an aqueous suspension by the addition of water provide the combined active ingredients in admixture with a dispersing or wetting agent, suspending agent and one or more preservatives. Suitable sweetening, flavouring and colouring agents may also be present.

The combined pharmaceutical compositions of the invention may also be in the form of oil-in-water emulsions. The oily phase may be a vegetable oil, for example olive oil or arachis oil, or a mineral oil, for example liquid paraffin, or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative, flavouring and colouring agents.

Suspensions and emulsions may contain a carrier, for example a natural gum, agar, sodium alginate, pectin, methylcellulose, carboxymethylcellulose, or polyvinyl alcohol.

In a preferred embodiment, 6-{4-[1-(Propan-2-yl)piperidin-4-yl]-1,4-diazepan-1-yl}-N-(pyridin-4-yl)pyridine-2-carboxamide is to be administered via the oral route. Such compositions may be produced using conventional formulation techniques. In particular, spray-drying may be used to produce microparticles comprising the active agent dispersed or suspended within a material that provides the controlled release properties.

The process of milling, for example jet milling, may also be used to formulate the therapeutic composition. The manufacture of fine particles by milling can be achieved using conventional techniques. The term "milling" is used herein to refer to any mechanical process which applies sufficient force to the particles of active material to break or grind the particles down into fine particles. Various milling devices and conditions are suitable for use in the production of the compositions of the invention. The selection of appropriate milling conditions, for example, intensity of milling and duration, to provide the required degree of force, will be within the ability of the skilled person. Ball milling is a preferred method. Alternatively, a high pressure homogeniser may be used, in which a fluid containing the particles is forced through a valve at high pressure, producing conditions of high shear and turbulence. Shear forces on the particles, impacts between the particles and machine surfaces or other particles, and cavitation due to acceleration of the fluid, may all contribute to the fracture of the particles. Suitable homogenisers include the EmulsiFlex high pressure homogeniser, the Niro Soavi high pressure homogeniser and the Microfluidics Microfluidiser. The milling process can be used to provide the microparticles with mass median aerodynamic diameters as specified above. If hygroscopic, the active agent may be milled with a hydrophobic material, as stated above.

If it is required, the microparticles produced by the milling step can then be formulated with an additional excipient. This may be achieved by a spray-drying process, e.g. co-spray-drying. In this embodiment, the particles are suspended in a solvent and co-spray-dried with a solution or suspension of the additional excipient. Preferred additional excipients include polysaccharides. Additional pharmaceutically effective excipients may also be used.

Compositions intended for inhaled, topical, intranasal, intravenous, sublingual, rectal and vaginal use may be prepared according to any method known to the art for the manufacture of pharmaceutical compositions.

Therapy according to the invention may be conducted in generally known manner, depending on various factors, such as the sex, age or condition of the patient, and the existence or otherwise of one or more concomitant therapies. The patient population may be important.

Therapy according to the invention may be administered selectively based on determining whether a tissue sample has a high level of SDF-1; and selectively administering to a human or animal patient in need thereof 6-{4-[1-(Propan-2-yl)piperidin-4-yl]-1,4-diazepan-1-yl}-N-(pyridin-4-yl)pyridine-2-carboxamide in any suitable form and an immune checkpoint inhibitor in sufficient amounts to provide a therapeutic effect, based on said subject having the tissue sample having been previously determined to have a high level of SDF-1. Those skilled in the art know techniques and methods used for determining the level of SDF-1. For example, SDF-1 expression may be determined by RNA sequencing and may be expressed as fragments read per million mapped reads per kilobase of transcript (FPKM). FPKM may be normalised to all the fragments read and to the length of the genes, and so is in effect a ratio of the number of SDF-1 reads to all the other genes read multiplied by one million. An increased or high SDF-1 level may be greater than 3 FPKM. A high level of SDF-1 may be at least 4, or at least 10, or at least 11, or at least 12, or at least 13, or at least 14, or at least 15, or at least 16 FPKM. A high level of SDF-1 may be at least 17, or at least 26 or at least 42 FPKM.

The present invention is based at least in part on the following in vivo studies.

Study 1

GL261-luc2 cells ($1 \times 10^5$) are injected stereotactically into the striatum of female C57Bl/6 mice. 8 mice per cohort. After the tumours have grown (3-6 days) to equivalent size detected by bioluminescence, the mice are randomised and subjected to treatments with immune checkpoint inhibitor alone or immune checkpoint inhibitor with 6-{4-[1-(Propan-2-yl)piperidin-4-yl]-1,4-diazepan-1-yl}-N-(pyridin-4-yl)pyridine-2-carboxamide.

6-{4-[1-(Propan-2-yl)piperidin-4-yl]-1,4-diazepan-1-yl}-N-(pyridin-4-yl)pyridine-2-carboxamide is administered at a dosage of 50 mg/kg, 5 days out of 7 for the duration of the experiment. The checkpoint inhibitors used in the experiment are antibodies against mouse PD1 and CTLA4, dosed i.p. once every three days at 250 microg per dose. Alternative checkpoint inhibitors used in the study are antibodies against mouse PD-L1 and PD-L2, also dosed i.p. once every three days at 250 microg per dose.

The preliminary experimental studies indicate that combinations of 6-{4-[1-(Propan-2-yl)piperidin-4-yl]-1,4-diazepan-1-yl}-N-(pyridin-4-yl)pyridine-2-carboxamide and an immune checkpoint inhibitor have significantly improved efficacy in tumour treatment in animals when compared to 6-{4-[1-(Propan-2-yl)piperidin-4-yl]-1,4-diazepan-1-yl}-N-(pyridin-4-yl)pyridine-2-carboxamide monotherapy and immune checkpoint inhibitor monotherapy.

Study 2

Four syngeneic cell lines (EMT-6, H22, CT26, B16F10small) were cultured and when in exponential growth were inoculated in mice subcutaneously with tumour cells in 0.1 mL of PBS for tumour development. After the mean tumour size reached approximately 80-120 mm$^3$ the mice were treated with anti-PD1 antibody (clone RMP1-14) (10 mg/kg i.p. twice weekly for 3 weeks) or 6-{4-[1-(Propan-2-yl)piperidin-4-yl]-1,4-diazepan-1-yl}-N-(pyridin-4-yl)pyridine-2-carboxamide (50 mg/kg p.o. 5 days out of 7), or a combination of the two treatments. Tumour volumes were measured twice weekly at least in two dimensions using a caliper, and the volume expressed in mm$^3$ using the formula: V=0.5 a×b$^2$ where a and b are the long and short diameters of the tumour, respectively. Tumour growth was measured and inhibition of tumour growth reported in comparison to a vehicle treated group. All groups contained 8 mice. If the tumours in a group reached an average volume of 2000 mm$^3$, the experiment was terminated.

SDF-1 levels were measured by RNA sequencing and are expressed as fragments read per million mapped reads per kilobase of transcript (FPKM). FPKM is normalised to all the fragments read and to the length of the genes, and so is in effect a ratio of the number of SDF-1 reads to all the other genes read multiplied by one million.

Results are presented in Table 1 below.

TABLE 1

| Tumour type | Cell line | SDF-1 level (FPKM) | % inhibition of tumour growth relative to control | | |
|---|---|---|---|---|---|
| | | | 641 | Anti-PD1 | Combination |
| Breast | EMT6 | 42 | 79.8 | 62 | 98 |
| Liver | H22 | 26 | 20.1 | 72.1 | 87.1 |
| Colorectal | CT26 | 17 | 32.1 | 22.7 | 53.1 |
| Melanoma | B16F10 small | 4 | 0 | 1 | 24.1 |

641: treatment with 6-{4-[1-(Propan-2-yl)piperidin-4-yl]-1,4-diazepan-1-yl}-N-(pyridin-4-yl)pyridine-2-carboxamide alone; Anti-PD1: treatment with anti-PD1 antibody alone; Combination: combined treatment.

The combination data reveals an effect that is greater than the statistically expected additive effect of 641 and anti-PD1. Therefore, it can be said that there is a surprisingly synergistic effect of anti-PD1 antibodies with 6-{4-[1-(Propan-2-yl)piperidin-4-yl]-1,4-diazepan-1-yl}-N-(pyridin-4-yl)pyridine-2-carboxamide, in which the combination inhibits tumour growth significantly more than anti-PD1 antibodies alone.

The effect is shown in all of the above cell lines. An inhibition effect is shown in all samples with SDF-1 levels of 4 FKPM or greater.

The invention claimed is:

1. A composition comprising:
   (i) 6-{4-[1-(Propan-2-yl)piperidin-4-yl]-1,4-diazepan-1-yl}-N-(pyridin-4-yl)pyridine-2-carboxamide; and
   (ii) an immune checkpoint inhibitor,
   wherein the immune checkpoint inhibitor is an anti-PD-1 antibody.

2. A method of treating a tumour in a subject comprising administering to the subject 6-{4-[1-(Propan-2-yl)piperidin-4-yl]-1,4-diazepan-1-yl}-N-(pyridin-4-yl)pyridine-2-carboxamide and an immune checkpoint inhibitor in sufficient amounts to provide a therapeutic effect,
   wherein the immune checkpoint inhibitor is an anti-PD-1 antibody.

3. The method of claim 2, wherein said administration is selectively based on said subject having a tumour having a level of SDF-1 that is greater than 3 FPKM.

4. The method of claim 2, wherein said administration is selectively based on said subject having a tumour having a level of SDF-1 that is greater than 10 FPKM.

5. The method of claim 2, wherein the immune checkpoint inhibitor is administered simultaneously with 6-{4-[1-(Propan-2-yl)piperidin-4-yl]-1,4-diazepan-1-yl}-N-(pyridin-4-yl)pyridine-2-carboxamide.

6. The method of claim 5, wherein the immune checkpoint inhibitor and 6-{4-[1-(Propan-2-yl)piperidin-4-yl]-1,4-diazepan-1-yl}-N-(pyridin-4-yl)pyridine-2-carboxamide is combined in a composition.

7. The method of claim 2, wherein the immune checkpoint inhibitor is administered separately with 6-{4-[1-(Propan-2-yl)piperidin-4-yl]-1,4-diazepan-1-yl}-N-(pyridin-4-yl)pyridine-2-carboxamide.

8. The method of claim 2, wherein the immune checkpoint inhibitor is administered sequentially with 6-{4-[1-(Propan-2-yl)piperidin-4-yl]-1,4-diazepan-1-yl}-N-(pyridin-4-yl)pyridine-2-carboxamide.

9. The method of claim 2, wherein the tumour is a cancer of an organ selected from the group consisting of esophagus, colon, rectum, breast, lung, endometrium, pancreas, skin, bladder, liver, kidney, gall bladder and ovary.

10. The method of claim 2, wherein the tumour is melanoma.

* * * * *